(12) United States Patent
Schlechter et al.

(10) Patent No.: US 10,430,773 B2
(45) Date of Patent: Oct. 1, 2019

(54) METHOD FOR DETERMINING THE STATE OF ACCESS CONTROL DEVICES AND SALES OR PAYMENT MACHINES OF AN ACCESS CONTROL SYSTEM

(71) Applicant: SKIDATA AG, Grödig/Salzburg (AT)

(72) Inventors: Thomas Schlechter, Seekirchen am Wallersee (AT); Thomas Buchegger, Dietach (AT); Markus Pichler, Kematen an der Krems (AT); Clemens Hesch, Linz (AT)

(73) Assignee: SKIDATA AG, Grödig/Salzburg (AT)

( * ) Notice: Subject to any disclaimer, the term of this patent is extended or adjusted under 35 U.S.C. 154(b) by 239 days.

(21) Appl. No.: 15/393,579

(22) Filed: Dec. 29, 2016

(65) Prior Publication Data
US 2017/0193482 A1    Jul. 6, 2017

(30) Foreign Application Priority Data
Dec. 30, 2015   (EP) .................................... 15203057

(51) Int. Cl.
| | |
|---|---|
| *G08B 1/00* | (2006.01) |
| *G06Q 20/20* | (2012.01) |
| *G01N 29/14* | (2006.01) |
| *G06Q 10/00* | (2012.01) |

(Continued)

(52) U.S. Cl.
CPC .......... *G06Q 20/206* (2013.01); *G01N 29/14* (2013.01); *G06Q 10/20* (2013.01); *G07F 9/026* (2013.01);
(Continued)

(58) Field of Classification Search
CPC ........ G06Q 20/32; G06Q 20/08; H04B 11/00; G08B 1/00
(Continued)

(56) References Cited

U.S. PATENT DOCUMENTS

| | | |
|---|---|---|
| 5,309,379 A | 5/1994 | Rawlings et al. |
| 5,945,602 A | 8/1999 | Ross |

(Continued)

FOREIGN PATENT DOCUMENTS

| | | |
|---|---|---|
| EP | 0851394 A1 | 7/1998 |
| WO | 9009644 A1 | 8/1990 |

OTHER PUBLICATIONS

European Search Report issued in corresponding European Patent Application No. 15203057.3 dated Jun. 8, 2016.

*Primary Examiner* — Oluseye Iwarere
*Assistant Examiner* — Seye Iwarere
(74) *Attorney, Agent, or Firm* — Michael J. Bujold; Davis & Bujold, P.L.L.C.

(57) ABSTRACT

A method for determining the state of access control devices and sales or payment machines of an access control system by detecting sound profiles emitted during operation by a component or component group by at least one microphone. Based upon the recorded sound profile, an acoustic identification signature is created in a server or a central computer, which identification signature is based on the frequency spectrum of the recorded sound profile and/or the temporal change thereof. The acoustic identification signature is compared with a reference identification signature(s) stored in the server and assigned to a component or a component group. In the event of the detecting an acoustic identification signature which exceeds a predetermined first threshold value, increased wear of the component or the component group is detected, while if the deviation exceeds a second threshold value, a defect of the component or the component group is defected.

9 Claims, 1 Drawing Sheet

(51) Int. Cl.
*G10L 17/00* (2013.01)
*G10L 17/04* (2013.01)
*G10L 17/06* (2013.01)
*G10L 17/22* (2013.01)
*G07F 9/02* (2006.01)

(52) U.S. Cl.
CPC ............ *G10L 17/005* (2013.01); *G10L 17/04* (2013.01); *G10L 17/06* (2013.01); *G10L 17/22* (2013.01)

(58) Field of Classification Search
USPC ................................. 705/18, 42, 39; 340/531
See application file for complete search history.

(56) References Cited

U.S. PATENT DOCUMENTS

| | | | |
|---|---|---|---|
| 9,400,977 B2* | 7/2016 | Brown | G06Q 20/3227 |
| 9,547,300 B2* | 1/2017 | Angerer | B21D 5/00 |
| 2004/0031856 A1* | 2/2004 | Atsmon | G06F 21/34 |
| | | | 235/492 |
| 2009/0091441 A1 | 4/2009 | Schweitzer, III et al. | |
| 2010/0063776 A1 | 3/2010 | Kayani | |
| 2010/0076793 A1* | 3/2010 | Goldstein | G06F 21/10 |
| | | | 705/4 |
| 2014/0309806 A1* | 10/2014 | Ricci | B60Q 1/00 |
| | | | 701/1 |
| 2015/0178878 A1* | 6/2015 | Huang | G06Q 50/34 |
| | | | 705/26.7 |
| 2015/0262162 A1* | 9/2015 | Akashika | G06Q 20/0655 |
| | | | 705/42 |
| 2015/0310416 A1* | 10/2015 | Akashika | G06Q 20/32 |
| | | | 705/39 |
| 2016/0065888 A1* | 3/2016 | Matsubara | G11B 27/34 |
| | | | 386/249 |
| 2017/0006028 A1* | 1/2017 | Tunnell | H04L 63/0861 |
| 2017/0011406 A1* | 1/2017 | Tunnell | G06Q 20/40145 |
| 2017/0193482 A1* | 7/2017 | Schlechter | G01N 29/14 |
| 2017/0323278 A1* | 11/2017 | Unnerstall | G06Q 20/18 |

* cited by examiner

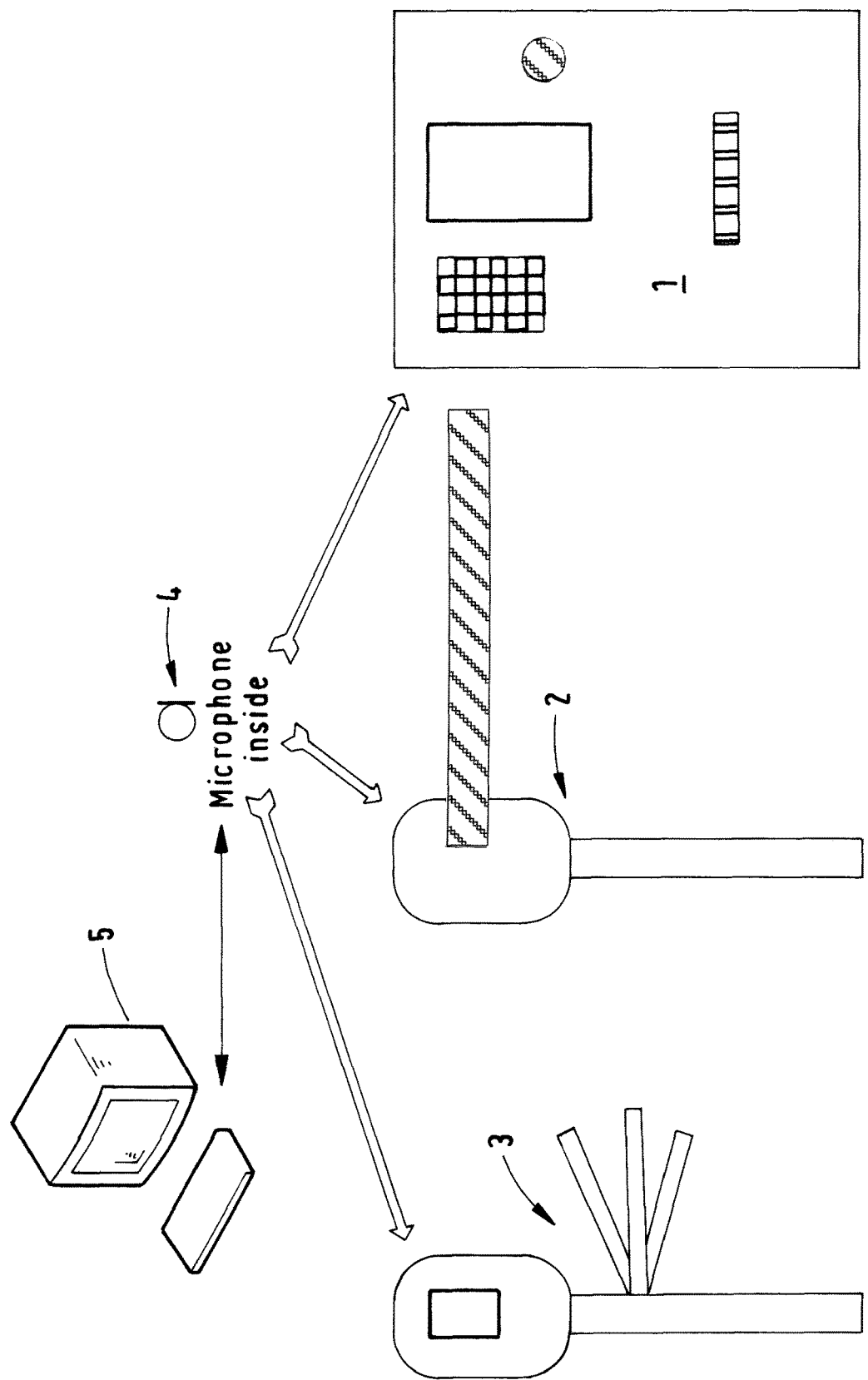

METHOD FOR DETERMINING THE STATE OF ACCESS CONTROL DEVICES AND SALES OR PAYMENT MACHINES OF AN ACCESS CONTROL SYSTEM

This application claims priority from European patent application serial no. 15203057.3 filed Dec. 30, 2015.

FIELD OF THE INVENTION

The present invention relates to a method, for determining the state of access control devices and sales or payment machines of an access control system.

BACKGROUND OF THE INVENTION

An access control system for vehicles or people Generally comprises a plurality of access control devices, which have a reading unit for reading the data required for checking the validity of an access authorization and a blocking device, which is actuated by an actuator controlled, by a control in order to allow a person or a vehicle to enter or to leave a building or a site. Furthermore, access control systems comprise sales machines for the access authorizations and/or payment machines for paying the fee for the use of the access control system. Payment machines are generally provided in the case of access control devices for motor vehicles, for example in multi-storey car parks.

In addition to electronic components, the above-mentioned access control devices or sales or payment machines of an access control system also comprise a plurality of mechanical components, such as for example blocking devices, which are transferred from a blocking position into a released position upon reading a valid access authorization, or coin return modules comprising conveyor belts for transporting the coins used as change, banknote input and output modules, ticket or credit card infeed modules, printer modules for access authorizations or electric motors for driving the components which can be actuated mechanically. Furthermore, fans are provided for dissipating the heat created during operation or the components.

For the access control devices or sales or payment machines of an access control system, predetermined maintenance intervals are generally prescribed in order to prevent a failure during operation. Nonetheless, individual components of these devices may be exposed to higher loading than expected, which may lead in a disadvantageous manner to increased wear and as a next step, to a failure of these components between two regular maintenance dates. Furthermore, on a case-by-case basis a fixed maintenance interval may be extended or adjusted to real-life conditions if lower wear than usual is present. Furthermore, maintenance-free access control devices or sales or payment machines of access control systems are known from the prior art, so that a timely detection of defects or increased wear is of particular importance for the operation of the access control system.

SUMMARY OF THE INVENTION

The present invention is based on the object of specifying a method for determining the state of access control devices and sales or payment machines of an access control system, the carrying out of which method means that wear of components, which may lead to a failure of the components, is detected in a timely manner. Furthermore, it should also be possible to determine by means of the method according to the invention, in the case of failure of an access control device or a sales or payment machine of an access control system, which component has a defect. vandalism attempts should additionally be detected.

Accordingly, a method for determining the state of access control devices and sales or payment machines of an access control system is suggested, in the context of which the sound profile in the audible or ultrasonic range emitted during operation by a component or component group of an access control device or a sales or payment machine of an access control system is detected permanently or in predetermined time intervals by at least one microphone and on the basis of the recorded sound profile, an acoustic identification signature is created in a server or central computer, which identification signature is based on the frequency spectrum of the recorded sound profile and/or the temporal change thereof, wherein the acoustic identification signature is assigned to a component or component group and is compared with an acoustic reference identification signature which is stored in the server and assigned to this component or component group, and wherein in the event of the detection of a deviation of the detected acoustic identification signature from the acoustic reference identification signature stored in the server, which deviation exceeds a predetermined first threshold value, increased wear of the component or the component group is detected, wherein if the deviation of the detected acoustic identification signature from the acoustic reference identification signature stored in the server exceeds a second threshold value, which is higher than the first threshold value, a defect of the component or the component group is detected.

BRIEF DESCRIPTION OF THE DRAWING

The invention is explained in detail with reference to the appended FIG. which is a diagram of a possible embodiment of the method.

DETAILED DESCRIPTION OF THE PREFERRED EMBODIMENTS

The at least one microphone can be arranged inside or outside an access control device or a sales or payment machine of an access control system. In the example shown in the FIGURE, a payment machine 1, an access control device 2 for vehicles and an access control device 3 for vehicles realized as a turnstile are illustrated, wherein at least one microphone 4 is arranged inside these devices in each case. A server in which an acoustic identification signature is created on the basis of the recorded sound profile is provided with the reference number 5 in the FIGURE.

The predetermined intervals of detection of the sound profile emitted during operation are chosen in such a manner that the sounds emitted by all components or component groups during operation are detected.

The assignment of a detected identification signature to a component or component group takes place according to an embodiment of the invention on the basis of characteristic properties of the sound profile emitted by the component or component group.

Alternatively, the assignment of a detected identification signature to a component or component group can take place in that, on the basis of the known precise sequence of the individual operations during the operation of an access control device or a sales or payment machine of am access control system, the detected identification signature is uniquely assigned to one operation and therefore one component or one component group, wherein the start of operation of the access control, device or the sales or payment machine is detected on the basis of the signals delivered by at least one microphone.

In the context of a development of the invention, the access control devices and sales or payment machines of an access control system are connected to the server for the purpose of data communication, wherein the information about which component or component group is active is transmitted to the server in real time, so that the assignment of a detected identification signature to a component or component group takes place in this manner.

It may optionally be provided that in the event of detection of a deviation of the detected acoustic identification signature from the acoustic reference identification signature stored in the server, which deviation exceeds the predetermined first threshold value, increased wear of the component or the component group is detected, and that if the deviation of the detected acoustic identification signature from the acoustic reference identification signature stored in the server exceeds the second threshold value, a defect of the component or the component group is detected if the respective threshold values are always exceeded for a predetermined time interval.

An acoustic identification signature can be calculated from the recorded sound profile or measured signal by means of the following steps for example:
1. Division of the measured signal into N successive part blocks;
2. for all N part blocks of the signal:
   a. Subtraction of the mean value (zero-mean adjustment);
   b. Fast Fourier transform (FFT) of the signal;
   c. Normalization by division by the sum of the absolute values of the spectral values;
3. Calculation of the average spectrum of all N spectra of the part blocks; and
4. Moving average smoothing of the average spectrum in the frequency range.

An acoustic identification signature can for example be compared with the acoustic reference identification signature stored in the server in that the pointwise differences in the frequency spectrum are added up in order to obtain a deviation measure. The reference identification signature of a component or a component group corresponds to the acoustic identification signature of this component or component group in a defect-free state with very low or without wear.

Alternatively, the creation of an acoustic identification signature from the recorded sound profile or measured signal may be based on the extraction and subsequent selection of a defined set of signal properties. Properties which come into question for this are e.g. properties from the time range, such as for example the energy content of the signal within a short defined time window (short-term energy), spectral properties, such as e.g. the spectral centre of gravity of the signal (spectral centroid) or the current spread around a frequency range (spectral spread), band energies, wherein the spectrum is divided into defined frequency bands, within which the available energy of the signal is calculated and what are known as Mel frequency cepstral coefficients (MFCC coefficients), which are known from speech recognition and lead to a compact representation of the frequency spectrum. The calculation of these coefficients is described comprehensively in the literature and is well-known for the person skilled in the art.

Subsequently, an investigation is carried out into which of the obtained above-described properties contribute least to the clear delimitation of the reference data of the signal. In addition, an investigation is carried out into how well the current set of signal properties allows a differentiation of individual recorded, signals or sound profiles, wherein in a next step, the least relevant property is removed from observation. The above steps are subsequently carried out anew until ultimately at one point, instead of an improvement of the result there is a deterioration of the result. At this point, all superfluous properties have then been eliminated. Although further thinning out would further reduce the overall complexity, it would also not optimally utilize the performance of the system. As a result, a set of signal properties is created which is optimal for a predetermined area of application, in the present, case for the identification signatures of access control devices and sales or payment machines of an access control system, and does not have to be derived anew again in subsequent steps.

An acoustic identification signature can for example here be compared with the acoustic reference identification signature stored in the server in that the pointwise differences of the signal properties of the set of signal properties, which is optimal for a predetermined area of application, are added up in order to obtain a deviation measure.

In the context of a learning phase, the usual sounds during operation of an intact access control device or a sales or payment machine of an access control system are recorded by the at least one microphone, wherein in this manner, the recorded sound signals are in each case assigned uniquely to one operation and thus one component or one component group, which is involved in the operation, in the server, taking account of the known precise sequence of the individual operations of the access control device or the sales or payment machine, and wherein acoustic reference identification signatures for the components or component groups are created from the recorded sound signals and stored in the server. If for example according to the workflow in a payment machine, coin insertion in particular is active, the recorded signals are to be assigned to the components active during coin insertion, such as the coin slot lock, coin validation, etc. If according to the workflow, a card, for example a credit card is fed in, then the sound signals are assigned to the components of the card indeed. The beginning of the operation of the access control device or the sales or payment machine is detected on the basis of the signals delivered by at least one microphone, so that whilst taking account of the known precise sequence of the individual operations after the beginning of operation, the assignment of the recorded sound signals and thus the reference identification signatures to the components or component groups takes place.

If the access control devices and sales or payment machines of an access control system are connected to the server for the purpose of data communication and the information about which component or component group is active is transmitted to the server in real time, the learning phase takes place in that the usual sounds during operation of an intact access control device or a sales or payment machine of an access control system are recorded by the at least one microphone, which sounds are assigned in the server to the currently active component or component group in each case; subsequently the corresponding reference identification signature is created in the server.

Furthermore, according to a development of the invention, conventional ambient sounds are also recorded and stored as standard background noise.

If a few components of the machine are always only activated simultaneously with other components as a component group, it can first be detected according to the method that at least one component of this component group is defective.

In order to increase the accuracy of the method, at least one microphone can be assigned to each component, which microphone is arranged in the interior of the access control device or the sales or payment machine of an access control system, e.g. in a sales machine, or externally. In this case, the assignment of a detected identification signature to a component can take place in that the underlying sound profile recorded by a microphone is assigned to the component to which the microphone is assigned.

In the context of a development of the invention, in addition to an acoustic reference identification signature for a component or a component group, identification signatures are stored in the server, which in each case correspond to an actual defect of a component or a component group. In this manner, an identification signature not corresponding to the reference identification signature can, in the case of adequate matching with an identification signature assigned to an actual defect of a component or a component group, be assigned to the respective defect of a component or a component group, so that directly suitable measures can be introduced directly. For example, a specialized technician can inspect the device on site in a targeted manner and, if necessary, replace components. These signatures are added to the data record assigned to a component or a component group when the actual defects are occurring for the first time.

An adequate match is present if the deviation of the detected acoustic identification signature from the acoustic identification signature stored in the server falls below a third predetermined threshold value.

According to the invention, in the case of detected identification signatures, which correspond neither to the reference identification signature nor to an identification signature assigned to a defect of a component or a component group, these identification signatures are stored in the server as new identification signatures, which correspond to a not yet classified or categorized defect, wherein the classification or categorization then takes place when the defect has been identified.

It is possible by means of the concept according to the invention to detect in a timely manner whether a component should be replaced or whether an unscheduled lubrication is required, etc.

In the context or a further embodiment of the invention, in the event of a detected identification signature, which cannot be assigned to a component or component group or the deviation of which exceeds the second threshold value of ail acoustic reference identification signatures and cannot correspond to a defect of a component or component group, which can be determined for example on the basis of intensity and point of origin, a vandalism attempt or application of force may be detected.

Analogously, strong rain or strong wind can be detected on the basis of a detected identification signature, which may necessitate a temporary deactivation of a device in order to prevent damage. For this purpose, reference signatures are stored in the server, which correspond to strong rain or strong wind.

For example, an access control device for vehicles comprising a barrier boom can be deactivated in the event of the detection of an identification signature, which corresponds to strong wind, in order to prevent damage to the arriving vehicles due to the wind. Furthermore, in the event of the detection of strong rain, sensitive components, for example the ticket infeed of a payment machine, can be covered by means of a suitable device in order to prevent damage due to the rain.

The invention claimed is:

1. A method of determining a state of access control devices and sales or payment machines of an access control system, the method comprising:
   detecting, permanently or in predetermined time intervals, a sound profile in an audible or an ultrasonic range emitted during operation by a component or a component group of an access control device or a sales or payment machine of an access control system by at least one microphone and on a basis of a recorded sound profile,
   creating an acoustic identification signature in a server or a central computer, which identification signature is based on a frequency spectrum of the recorded sound profile and/or a temporal change thereof,
   assigning the acoustic identification signature to a component or a component group and comparing with an acoustic reference identification signature which is stored in the server and assigned to the component or component group,
   in an event of detection of a deviation of the detected acoustic identification signature from the acoustic reference identification signature stored in the server, which deviation exceeds a predetermined first threshold value, detecting increased wear of the component or the component group, and
   in an event of detection of the deviation of the detected acoustic identification signature from the acoustic reference identification signature stored in the server, which deviation exceeds a second threshold value, which is higher than the first threshold value, detecting a defect of the component or the component group.

2. The method of determining the state of access control devices and sales or payment machines of the access control system according to claim 1, further comprising recording, in a context of a learning phase, usual sounds during operation of an intact access control device or an intact sales or payment machine of an access control system by the at least one microphone, assigning the recorded sound signals are, in each case, to one component or one component group, and creating acoustic reference identification signatures, for the components or component groups, from the recorded sound signals and stored in the server, assignment of the recorded sound signals and thus the reference identification signatures to the components or component groups takes place in that the beginning of the operation of the access control device or the sales or the payment machine is detected on the basis of the signals delivered by at least one microphone, wherein, taking account of a known precise sequence of the individual operations of the access control device or a sales or payment machine, the recorded sound signals are, in each case, assigned uniquely to one operation and thus one component or one component group, or takes place in that the access control devices and sales or payment machines of the access control system are connected to the server for the purpose of data communication and the information about which component or component group is active is transmitted to the server in real time so that the recorded sound signals are assigned, in the server, to the currently active component or component group in each case.

3. The method of determining the state of access control devices and sales or payment machines of the access control system according to claim 1, further comprising storing identification signatures, in addition to an acoustic reference identification signature for a component or a component group, in the server which, in each case, correspond to an actual defect of a component or a component group, an identification signature not corresponding to the reference identification signature can, in a case of adequate matching with an identification signature corresponding to an actual defect of a component or a component group, be assigned to the respective defect of a component or a component group directly.

4. A method of determining a state of access control devices and sales or payment machines of an access control system, the method comprising:

detecting, permanently or in predetermined time intervals, a sound profile in an audible or an ultrasonic range emitted during operation by a component or a component group of an access control device or a sales or payment machine of an access control system by at least one microphone and on a basis of a recorded sound profile, creating an acoustic identification signature in a server or a central computer, which identification signature is based on a frequency spectrum of the recorded sound profile and/or a temporal change thereof, assigning the acoustic identification signature to a component or a component group and comparing with an acoustic reference identification signature which is stored in the server and assigned to the component or component group, in an event of detection of a deviation of the detected acoustic identification signature from the acoustic reference identification signature stored in the server, which deviation exceeds a predetermined first threshold value, detecting increased wear of the component or the component group, in an event of detection of the deviation of the detected acoustic identification signature from the acoustic reference identification signature stored in the server, which deviation exceeds a second threshold value, which is higher than the first threshold value, detecting a defect of the component or the component group, storing identification signatures, in addition to an acoustic reference identification signature for a component or a component group, in the server which, in each case, correspond to an actual defect of a component or a component group, an identification signature not corresponding to the reference identification signature can, in a case of adequate matching with an identification signature corresponding to an actual defect of a component group, be assigned to the respective defect of a component of a component group directly, and in a case of detected identification signatures, which neither corresponds to the reference identification signature nor to an identification signature assigned to a defect of a component or a component group, storing these identification signatures in the server as new identification signatures, which correspond to a not yet classified or categorized defect, and classification or categorization the detected identification signatures when the defect is identified.

5. The method of determining the state of access control devices and sales or payment machines of the access control system according to claim 1, further comprising detecting a vandalism attempt or an application of force, in an event of a detected identification signature which cannot be assigned to a component or component group or a deviation of which exceeds the second threshold value of all acoustic reference identification signatures and cannot correspond to a defect of a component or component group.

6. The method of determining the state of access control devices and sales or payment machines of the access control system according to claim 1, further comprising storing reference signatures in the server, which correspond to strong rain or strong wind, and if strong rain or strong wind are detected on a basis of a detected identification signature, temporarily deactivating a device in order to prevent damage.

7. The method of determining the state of access control devices and sales or payment machines of the access control system according to claim 1, further comprising assigning a detected identification signature to a component or component group on a basis of characteristic properties of the sound profile emitted by the component or component group.

8. A method of determining a state of access control devices and sales or payment machines of an access control system, the method comprising:

detecting, permanently or in predetermined time intervals, a sound profile in an audible or an ultrasonic range emitted during operation by a component or a component group of an access control device or a sales or payment machine of an access control system by at least one microphone and on a basis of a recorded sound profile, creating an acoustic identification signature in a server or a central computer, which identification signature is based on a frequency spectrum of the recorded sound profile and/or a temporal change thereof, assigning the acoustic identification signature to a component or a component group and comparing with an acoustic reference identification signature which is stored in the server and assigned to the component or component group, in an event of detection of a deviation of the detected acoustic identification signature from the acoustic reference identification signature stored in the server, which deviation exceeds a predetermined first threshold value, detecting increased wear of the component or the component group, in an event of detection of the deviation of the detected acoustic identification signature from the acoustic reference identification signature stored in the server, which deviation exceeds a second threshold value, which is higher than the first threshold value, detecting a defect of the component or the component group, and assigning a detected identification signature to a component or component group on a basis of a known precise sequence of the individual operations during the operation of an access control device or the sales or payment machine of the access control system, uniquely assigning the detected identification signature to one operation and therefore one component or one component group, and detecting the start of operation of the access control device or the sales or payment machine on a basis of the signals delivered by the at least one microphone.

9. The method of determining the state of access control devices and sales or payment machines of the access control system according to claim 1, further comprising connecting the access control devices and sales or payment machines to the server for data communication, actively transmitting the information about which component or component group to the server in real time so that the assignment of a detected identification signature to a component or component group takes place in this manner.

\* \* \* \* \*